United States Patent [19]

Korol et al.

[11] Patent Number: 4,820,292
[45] Date of Patent: Apr. 11, 1989

[54] ANTI-MICROBIAL SENSITIVITY TEST AND TESTING STRATUM

[75] Inventors: Bernard Korol, Highland Beach, Fla.; Paul Nathan, Cincinnati, Ohio

[73] Assignee: Enguay Pharmaceutical Associates, Boca Raton, Fla.

[21] Appl. No.: 199,379

[22] Filed: May 27, 1988

Related U.S. Application Data

[63] Continuation-in-part of Ser. No. 815,874, Jan. 3, 1986, Pat. No. 4,747,845, which is a continuation-in-part of Ser. No. 542,754, Oct. 17, 1983, Pat. No. 4,563,184.

[51] Int. Cl.$^4$ .......................... C08K 5/41; C08K 5/34; C08K 5/15; C08K 5/10
[52] U.S. Cl. ........................................ 435/32; 435/31; 435/32; 435/33; 604/368
[58] Field of Search ..................... 604/368; 435/31, 32, 435/33

[56] References Cited

U.S. PATENT DOCUMENTS 3,960,658 6/1976 Avakian et al. ........................ 435/33
4,311,794 1/1982 Melnick et al. ........................ 435/32

*Primary Examiner*—John Kight
*Assistant Examiner*—Carlos Azpuru
*Attorney, Agent, or Firm*—Paul M. Denk

[57] ABSTRACT

An anti-microbial sensitivity test and testing stratum is disclosed for evaluating the sensitivity of different anti-microbial agents relative to identifiable microbial contaminants. The test stratum comprises a polymer such as poly(2-hydroxyethylmethacrylate) referred to as PHEMA, an organic solvent, such as polyethylene glycol (PEG), a hydrogen binding plasticizer, such as dimethylsulfoxide (DMSO), an an anti-microbial agent such as silver sulfadiazine, mafenide, nystatin, nitrofurazone, silver nitrate, bacitracin, gentamicin, amphotericin B, cesium nitrate, or other anti-microbial agents. The test includes positioning testing stratum of the type described, each having a different anti-microbial agent therein, on a sterile plate or on an agar substrate and spaced in fixed relationship to one another. The testing stratum are self adhering and remain fixed on a sterile plate, or on an applicator, even when the sterile plate, is inverted. The testing stratum further provide a sustained release of the anti-microbial agent incorporated therein. The testing stratum are then subjected to samples from the wound site, often containing microbial contaminants, and after a predetermined period of incubation, evaluation indicative of microbial contamination can then be made and examination of the zones of inhibition over and around each of the anti-microbial testing stratum will determine effectiveness of each anti-microbial agent contained in the test system.

13 Claims, 3 Drawing Sheets

ANTI-MICROBIAL SENSITIVITY TEST AND TESTING STRATUM

CROSS REFERENCE TO RELATED APPLICATION

This application is a continuation-in-part application of the patent application filed by Bernard Korol, as a sole applicant, Ser. No. 815,874, filed on Jan. 3, 1986, now U.S. Pat. No. 4,747,845 and which application is denominated as a continuation-in-part of application having Ser. No. 542,754, filed Oct. 17, 1983, now U.S. Pat. No. 4,563,184, issued on Jan. 7, 1986, all of such applications and patent being owned by a common assignee.

BACKGROUND OF THE INVENTION

This invention relates principally to an anti-microbial sensitivity test and testing stratum, for determining the effectiveness/ineffectiveness of a variety of anti-microbial agents, or bactericides, any of which may be used in conjunction with the treatment of a particular skin surface or wound infection, and which infection may contain no identified, or an unidentified, microbial type of contaminant.

A variety of prior art is available in this particular field, for disclosing various diagnostic type of packages or means that are used for aiding the medical practitioner in the identification of the type of bacteria to be treated. But, initially, it must be commented herein that a co-inventor of this particular development, as can be seen from the cross reference to related application, is also the holder of U.S. Pat. No. 4,563,184, which identifies the base synthetic resin wound dressing and method of treatment using same, disclosing the type of polymer that is even used in conjunction with this current invention, whereas, in the identified patent, it has been used as a means for functioning as a wound dressing, and which may have incorporated therein various medicines, for treatment of burns, or other forms of wounds. In addition, the particular polymer disclosed in the earlier patent is related to, but obviously of different patentable structure, to the form of polymer that is shown in the earlier patent to Moro, et al, U.S. Pat. No. 4,272,518. In that particular patent, the polymer is applied as a paste, and when it sets up, forms a more hardened coating, for application to a wound, or other treatment area, without having the pliability, flexibility and adhesiveness of the synthetic resin disclosed in U.S. Pat. No. 4,563,184. Thus, when functioning in that manner, it is questioned whether the Moro style of resin could be used in conjunction with the current invention, since it is necessary to have some flexibility, and adhesiveness as well as drug release characteristics, in order to control microbial contaminants in the manner of this current invention.

The earlier patent to Forg, U.S. Pat. No. 2,904,474, describes a process and means for carrying out bacteriological operations. As can be seen, the device is used for taking samples for detecting certain types of bacteria in liquids, by utilizing a sterile flat-like structure made of an absorbent material, for absorbing bacteria, and for their immersion into a liquid for testing.

The patent to Reich, U.S. Pat. No. 2,985,288, discloses another form of diagnostic package, wherein sheets of paper-like material are capable of receiving centrally thereof a culture-absorbent material for use for testing purposes.

The patent to Fink, U.S. Pat. No. 3,474,004, discloses another form of disposable culture device. As can be seen, the microbic test device incorporates a plate for the culture medium, a cover, a holder, and a plurality of test elements therein, and provided upon the surface of the culture medium for providing testing.

The patent to Monaghan, U.S. Pat. No. 3,923,604, discloses tubular articles, of the type incorporating a housing having diagnostic swabs or similar devices contained therein, with the housing being breakable, to provide a release of the swab for application.

U.S. Pat. No. 4,014,746, to Greenspan, discloses another method of and apparatus for collecting cultures. This also is a form of swab, contained within an airtight chamber, and available for usage once the seal is broken.

The patent to Spinner, et al, U.S. Pat. No. 4,014,748, discloses an anaerobic culture collecting and transporting apparatus, comprising a swab, contained with a closable container, and having a collected culture receiving depot therein. The container also provides various culture medium, and chemical means within the container to selectively activate the culture once placed upon the depot.

The patent to Beckford, et al, U.S. Pat. No. 4,030,980, shows another form of apparatus and method for identification of selected clinical yeast. This particular device is another form of apparatus for identification of a number of the most frequently isolated medical yeast, and which employs a single tube and a multi-cavity plate, the tube containing the sterile, liquid media, to test the germ-tube production, while the plate contains a plurality of independently sealed peripheal wells, for deposition of the bacteria onto their deposited solid media for performance of select tests.

The patent to Miller, et al, U.S. Pat. No. 4,038,148, shows another form of anaerobic environmental system for bacteria culture testing.

The patent to Montagnon, U.S. Pat. No. 4,066,511, shows an analytic device and method, which is useful for the detection of unknown microrganism, such as bacterium in a liquid nutritive medium. As can be seen, though, the test strips utilized incorporates a liquid reactive surface which is quite distinct from the principle of structure and application of usage of the current invention.

The patent to Hirshaut, U.S. Pat. No. 4,072,577, discloses another method and miniaturized apparatus for cultivating bacteria. It appears that this particular apparatus incorporates various culture dishes, for holding select culture medium, for providing testing.

The patent to Wielinger, et al, U.S. Pat. No. 4,250,256, shows another form of microbiological test device, which utilizes a nutrient card, having covering layers thereover and which are permeable to nutrients, but impermeable to bacteria. This device appears to be just the opposite from what is intended to be achieved from the current invention.

The patent to Citri, U.S. Pat. No. 4,381,343, discloses another means for determination of anti-bacterial agents. As can be seen, apparently the test material utilized are starch-iodine strips of pad material, formed from a nutrient-agar plate.

Finally, the patent to Saxholm, U.S. Pat. No. 4,591,556, shows another form of apparatus and associated methods for use in microbiological, serological, immunological, clinical, chemical and similar laboratory work. In this particular instance, an active substance is contacted with a substrate, and is immersed in respective isolated substrate regions so that diffusion can take place, apparently for detecting and laboratory purposes.

In view of the foregoing, the current invention is more concerned with the formation of a particularly styled resin base, formed in the manner as described in this invention, to form small test discs, or the like, which may be previously treated with select antibacterial or antimicrobial agents, or bactericides, and provide for a reactive contact with any test specimen of bacteria or infection obtained from an infected surface wound or other source, to determine which of the antimicrobial drugs would be most useful for treatment of the affected person, animal, or the like.

SUMMARY OF THE INVENTION

Among the many objects and features of the present invention may be noted:

The provision of an anti-microbial sensitivity test and testing stratum for determining the effectiveness/ineffectiveness of a variety of anti-microbial agents relative to identified or identifiable microbial contaminants:

The provision of an anti-microbial sensitivity test and testing stratum which yield sensitive and specific determination of a variety of anti-microbial agents relative to a specific and identified microbial contaminant or contaminants;

The provision of anti-microbial sensitivity test and testing stratum for determining the anti-microbial drug-/agent of choice in the treatment of bacteria or fungi infections of the skin;

The provision of an anti-microbial sensitivity test and testing stratum which provides simultaneous in vitro testing of a variety of anti-microbial agents when subjected to microbial contaminants which are conditioned for growth, to simulate a wound site or the like;

The provision of an anti-microbial sensitivity test and testing stratum which enables an optimum amount for various anti-microbial agents to be determined relative to an identified microbial contaminant or contaminants, in order to detect activity/inactivity of the anti-microbial agents relative to the contaminant;

The provision of an anti-microbial test and testing stratum which may be incorporated into a diagnostic testing kit with other laboratory testing components, to facilitate use and testing thereof by a laboratory or individual users; and The provision of an antimicrobial sensitivity test and testing stratum which is simple to administer; in some instances enables paraprofessionals such as nurse practitioners to administer the test for patients in nursing homes and the like; can be quickly and easily evaluated within twenty-four (24) after the infection is sampled; can be used in lieu of extensive commercial laboratory testing with the same or better results and determined and used in-office; and is otherwise well adapted for the purposes intended. The provision of a sensitivity test for Silver Salts which are not readily released from standard paper discs.

DESCRIPTION OF PREFERRED EMBODIMENTS

Figure 1:
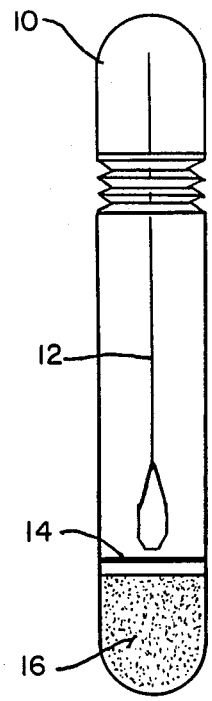
FIG. 1 is a combined illustration showing a front elevational view of a sealed culture tube with a premoistened saline swab therein, together with the procedural step used in the anti-microbial sensitivity test, in which the premoistened swab is removed from the culture tube and generally rubbed over the wound, and placed into a separate tube containing a small amount of other culture medium.

This continuation-in-part application claims copendent dependency upon U.S. Ser. No. 815,874, filed Jan. 3, 1986, which in turn, is denominated as having copendent dependency on U.S. Ser. No. 542,754, filed Oct. 17, 1983, now U.S. Pat. No. 4,563,184, issued on Jan. 7, 1986. Before discussing the specifics of the present invention, it is important to understand the interrelationship of the aforementioned copending applications to each other, in order to fully understand and appreciate the differences of the present invention disclosed herein.

In U.S. patent application Ser. No. 542,754, filed Oct. 17, 1983, now U.S. Pat. No. 4,563,184, issued on Jan. 7, 1986, there is disclosed and claimed a synthetic resin wound dressing and method of treatment using same. The synthetic resin wound dressing was disclosed as incorporating a polymer, such as poly(2-hydroxyethylmethacrylate), referred to as PHEMA, an organic solvent such as polyethylene glycol (PEG), and a hydrogen binding plasticizer, such as dimethylsulfoxide (DMSO). The thus compounded wound dressing, known by the acronym DIMAC, may be applied to the wound site in the form of a paste for the in situ curing or setting thereof, or the dressing may be preformed and then applied to the wound site. A variety of anti-microbial/drug agents may be incorporated into the synthetic resin, resulting in the time released administration of the drug agent to a burn wound site, or the like, which is covered by the wound dressing. Thus, a novel synthetic polymer matrix system was created exhibiting essential and significant improvements in physical and functional characteristics over prior related products, including the release of embodied drugs in an extended duration pattern.

In U.S. patent application Ser. No. 815,874, filed Jan. 3, 1986, a new configuration of the synthetic resin matrix system (DIMAC) was created, when mixed and embodied with selected pharmaceutical and chemical agents. This synthetic resin matrix drug/chemical system released the embodied agent at predetermined extended duration rate. Thus, a variety of new drugs were developed and embodied in the fabricated matrix system and administered by different modes of application including, but not limited to, oral, topical, rectal, subcutaneous implant, or organ-specific implant. These formulations and procedures could also be utilized in the storage and extended delivery of agricultural products, particularly herbicides, insecticides, and nutritional supplements.

The present invention is a further development and extension of the above-identified synthetic resin matrix system in that it also uses that system together with anti-microbial agents to provide an anti-microbial sensitivity test and testing stratum for sensitive and specific determination of the effectiveness/ineffectiveness of a variety of anti-microbial agents which are simultaneously subjected to an identified microbial contaminant (bacteria or fungi), whether from in-vitro or in vivo sources. The anti-microbial sensitivity test and testing stratum was primarily developed for drugs to be applied topically or for in-vitro test microbials. It is expected that these anti-microbial tests and testing stratum will reflect the drug effects on in-vivo microbial contaminants, as will be understood further in the description that is to follow.

Before proceeding with the discussion, several terms used frequently in the specification and claims will be defined to facilitate the understanding of the present invention. The term "stratum" is defined to mean any layer, film or deposit, either formed in situ or preformed as a layer or film for subsequent handling and use. The term "microbial" or "microbial contaminant" is defined to include any type of living micro-organism such as bacteria and fungi, developed from in-vitro laboratory tests, or from in-vivo sources. The term "anti-microbial sensitivity test" means a test which yields sensitive and specific determination of the effectiveness/ineffectiveness of a variety of anti-microbial agents. The term "anti-microbial agents" is defined to include any drug or compound used by itself or in conjunction with other pharmacological components, which is useful in inhibiting or preventing microbial growth, and includes the specific anti-microbial agents as disclosed herein, as well as other anti-microbial agents now or hereafter developed.

It is further important to note that the anti-microbial test is based, in part, on well known anti-microbial assay or evaluation tests. Thus, in the findings of Heggers, et al, in the paper entitled "Control of Burn Wound Sepsis: A Comparison of IN-VITRO Topical Antimicrobial Assays," presented at the Presidential Awards Ceremony of the American Burn Association 18th Annual Meeting, Apr. 10, 1986, it concludes that in-vitro topical anti-microbial assay or evaluation test, particularly Nathan's Agar Well Diffusion (NAWD) test, is most effective in predicting the susceptibility of bacteria to topical anti-microbials. As will be more apparent herein, the Nathan in-vitro topical anti-microbial assay or evaluation test (NAWD) is the basis, in part, for the anti-microbial sensitivity test of the present invention.

The testing stratum used with the anti-microbial sensitivity test may employ a modified form of synthetic resin matrix system, generally identified by the acronym "DIMAC", as disclosed and claimed in the aforementioned co-pending patent and applications. In its broadest sense, the DIMAC synthetic resin matrix system, representing the chemical components of the drug carrier and delivery system, includes a particulate, hydrophilic, water swellable polymer, an inert, non-toxic water miscible organic solvent, and a hydrogen bonding plasticizer. The anti-microbial agent is added while mixing all the other components in the DIMAC delivery and storage system The potential of DIMAC to serve as a matrix for drug storage and sustained drug delivery was realized by the chance observation that the addition of the hydrogen bonding plasticizer, dimethylsulfoxide, to the formulation containing the polymer, poly(2-hydroxyethylmethacrylate), and the organic solvent, polyethylene glycol-400, produced a synthetic polymer matrix system which exhibited essential and significant improvements in physical and functional characteristics over prior related products. With an embodied drug therein, the DIMAC synthetic matrix delivery system was shown to release the embodied drug in an extended duration pattern. Depending on the relative concentration of the components of the synthetic resin system, a progressively developing transparency of the resin film with an increase in elasticity and rebound from the resin results, and the surface of the resin will generally have a significantly increased surface adhesiveness resulting from the reactions of the added DMSO.

These last-described changes and physical characteristics of the resin system require longer to develop than is required for the initial "set up" to occur, that is, the time between the mixing of the components of the synthetic resin and the time for the occlusive, non-tacky film to appear on the surface with little or no adhesiveness to the touch. This delayed process of developing a transparent film with an increase in elasticity, rebound and surface adhesiveness is referred as curing. These features and characteristics of the DIMAC synthetic matrix delivery system are important in the anti-microbial sensitivity test and testing stratum of the present invention.

To facilitate diagnostic use and testing, the testing stratum of the present invention are preferably preformed as thin wafers or attached discs which include the synthetic resin matrix system with an anti-microbial agent of predetermined dosage incorporated therein. Because of self-adhesiveness, the discs naturally adhere and remain in place on the test plate. The testing stratum preferably includes a modified DIMAC mixture or formula composed of poly(2-hydroxyethylmethacrylate), (PHEMA), having about 40% by weight of a testing stratum or test disc; dimethylsulfoxide (DMSO) having about 0.1% by weight of the testing stratum or test disc; polyethylene glycol (PEG-400) having a variable concentration by weight of the testing stratum based on a variable percentage by weight of the anti-microbial agent which is incorporated along with the other aforementioned components in the testing stratum or test disc. The concentration of the anti-microbial agent in the mixture was prepared to approximate their dosages in cream or ointment which are used on burn wounds, for example. Each of the anti-microbial agents in the testing stratum or test disc has been tested to determine an optimum value for its effectiveness in the in-vitro test system, as is shown in the tables below.

In the tables listed below, various examples of the testing stratum or test discs were prepared employing the DIMAC synthetic resin matrix system together with an active anti-microbial agent incorporated therein The formulations and concentrations of the various components of the stratum that were evaluated and the results and conclusions from the use of the various formulations and concentrations in connection with the anti-microbial sensitivity procedure are also described below.

TABLE I

| General Composition of Discs* | |
|---|---|
| Material | Percent of Final Weight |
| Poly(2-hydroxyl ethylmethacrylate) | 40.0 |
| Dimethylsulfoxide | 0.1 |
| Polyethylene glycol-400 and Drug | Varied as listed in Table 2 |

TABLE II

| Composition of the Individual Discs Containing Test Agents as % Final Weight | | |
|---|---|---|
| Test Drug | PEG-400 | Drug |
| Silver sulfadiazine | 59 | 1 |
| Mafenide | 54.9 | 5 |
| Nystatin | 58.1 | 1.7** |
| Nitrofurazone | 59.7 | 0.2 |
| Silver nitrate | 59.4 | 0.5 |
| Bacitracin | 59.07 | 0.83*** |

*Each disc contains 40% by weight of PHEMA and 0.1% by weight of DMSO
**100,000 units nystatin/g disc
***500 units bacitracin/g disc.

Testing stratum or test discs which are formulated in accordance with the aforementioned Tables I and II have been used in connection with the following method or procedure employed for the anti-microbial sensitivity test of the present invention. It will be understood that the anti-microbial agents or test drugs employed are those primarily used in the treatment of burn or other external wounds. Therefore, the discussion that is to follow relates primarily to this particular application of the present invention.

With reference to the drawings, FIG. 1 of the present invention shows a sealed plastic culture tube 10 having a pre-moistened saline swab 12 therein, a frangible separator 14 which can be broken by pressure on side of tube 10, and a culture media 16. In intitiating the anti-microbial sensitivity test, the pre-moistened saline swab 12 is removed from the culture tube 10 and is gently rubbed over the wound to accumulate wound bacteria on the surface of the swab. Thereafter, the swab is replaced in the same or another tube containing the culture media 16. The culture media may be a solution of the powdered form of brain-heart-infusion media (37 g/L of $H_2O$), which may be provided as part of a diagnostic kit, as will be discussed below. The contaminated swab is submerged into the culture media and a length of the stick from the swab may be broken off and discarded in order to facilitate closing of the culture tube 10. Alternatively, another tube containing only the media may be used to culture the bacteria.

Figure 2:
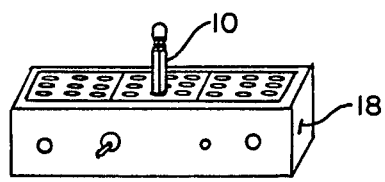
FIG. 2 is a heater block, of the type in which the tube may be located, or an incubator of the type in which the tube may be located, as at 30°-37° C., for a predetermined period of time.

Following the seeding of the culture media 16 with the microbial contaminant, FIG. 2 of the drawing shows the next step in the process as including the placement of the culture tube into a 30°–37° C. heater block 18 or the tube may be placed in a 30°–37° C. incubator for 3+ hours to incubate the culture media under conditions conducive to the growth of the microbial contaminant in the culture medium.

Figure 3:
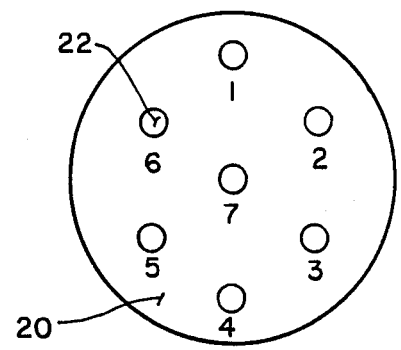
FIG. 3 is a further combined illustration showing a top elevational view of testing stratum impregnated with anti-microbial agents mounted on a Petri plate, together with the step of placing the impregnated testing stratum on the Petri plate and covering same with agar.

FIG. 3 shows DIMAC impregnated discs or testing stratum 22 which incorporate various anti-microbial agents that are placed on a sterile surface of a Petri plate or dish 20 and covered with agar. The test disc are self-adherent and thus stay in fixed position in spaced relationship relative to one another on the Petri plate or dish 20 shown in FIGS. 3. The anti-microbial components which were formulated in the various examples under test are identified by number and word description as follows:

No. 1. silver sulfadiazine
No. 2. mafenide
No. 3. nystatin
No. 4. nitrofurazone
No. 5. silver nitrate
No. 6. bacitracin
No. 7. control disc (no drug)

After the test disc or testing stratum are placed on the sterile Petri plate 20 and self-adhered thereto, brain-heart-infusion agar (52 g/L of $H_2O$) is preferably warmed to 95° C. and poured onto the sterile Petri plate. The agar is allowed to set for a period of 0.5 to 3± hours and form a thin gel across the surface of the Petri plate, while permitting the sustained release anti-microbial agent to be diffused into the agar around each of the test discs. In most cases, a Petri plate may be stable for a 24–72 hour period, although it is possible that the Petri plates with agar overlay may be used for up to 7 days after preparation, with some dating of the anti-microbial agent pattern forming around each test disc or stratum.

Figure 4:
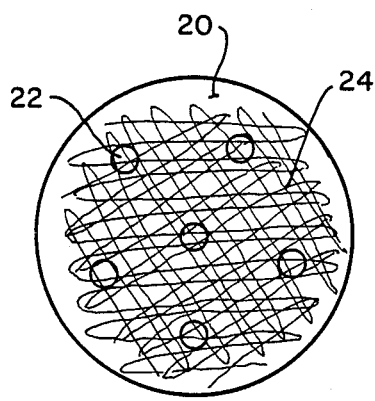
FIG. 4 is also a combined illustration showing the impregnated testing stratum mounted on a Petri plate, as in FIG. 3, with the contaminated culture media streaked over the plate, together with the step of streaking the Petri plate with the swabs containing the contaminated culture media, and incubating same for a predetermined time period at a predetermined temperature.

While the agar is allowed to set for 0.5 to 3± hours, the culture tube containing a microbial contaminant has also been incubated for the same interval, and is now ready to be applied to the agar treated surface of the Petri plate or dish. The culture media is removed from the heater block and then shaken or vortexed to mix the ingredients, and a second sterile pre-moistened saline swab is inserted into a media culture. The microbial contaminants on the second swab are smeared gently, but thoroughly, over the agar treated surface of the Petri plate, as shown at 24 in the FIG. 4 of the drawings. If desired, the original culture in media may be returned to the heater block for further growth of bacteria prior to testing on another test plate.

The plate containing the contaminated culture media is then inverted and incubated for about 16–24 hours at 30°–37° C. Following this, the plate is removed from the incubation chamber, and read or possibly returned to the incubator for an additional 18-24 hours if additional bacterial growth will clarify results on the plate.

When the Petri plate 20 is removed from the incubator, after suitable microbial contamination and incubation, a pattern of response around each of the test disc or testing stratum 22 should be clearly identifiable. Clear areas 26 around any of the test disc means that the microbial contamination are susceptible to the anti-microbial compound contained in the synthetic matrix delivery system. When bacteria grows over the test disc, the anti-microbial agent in the synthetic matrix delivery system is not effective against the microbial contaminant obtained from the wound. Possible variations in the observed pattern and their interpretation may include the following:

(1) Bacteria may go up to, but not over the disc. This indicates that the anti-microbial agent or drug is only slightly effective against the microbial contaminant.

(2) Two patterns may be around a disc including a clear region next to the test disc and an area with some bacterial growth surrounding the clear area. This pattern suggests that the active anti-microbial agent or drug killed the microbial contaminant when the agent is at a high concentration near the test disc, but when lesser amounts of the anti-microbial agent are available, the agent simply inhibits bacteria growth.

(3) A clearly visible pattern of reduced bacterial growth is seen around the test disc, but the region is not free of bacteria. This suggests a static effect of the active anti-microbial agent or drug on the microbial growth.

(4) Should the bacteria grow over the entire Petri plate, then none of the anti-microbial agents or drugs are active against the test bacteria.

Figure 5:
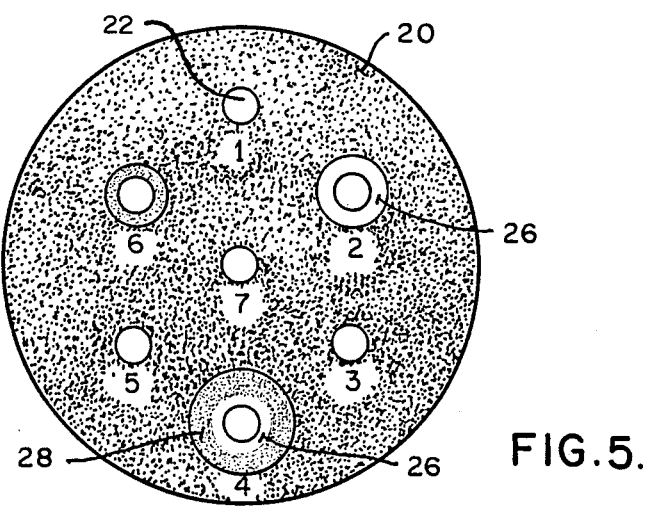
FIG. 5 is a further combined illustration showing a top plan view of the impregnated testing stratum on the Petri plate, with zones of inhibition, around certain of the testing stratum, together with the step of evaluating the impregnated testing stratum to determine the zones of inhibition around certain of the testing stratum to indicate anti-microbial activity.
Figure 6:
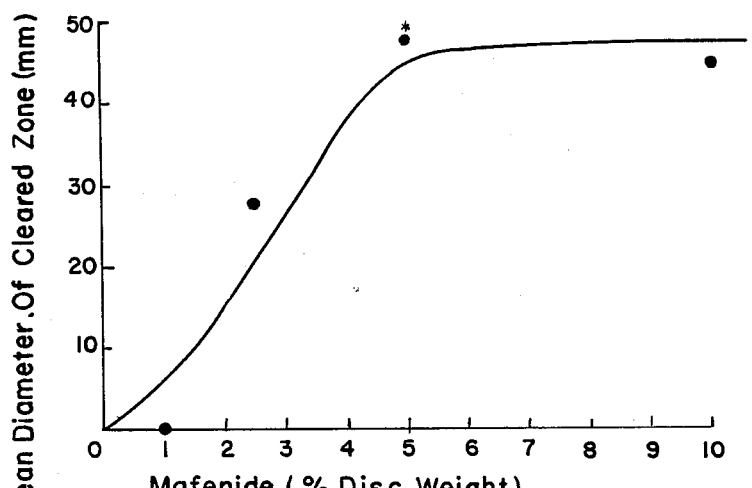
FIG. 6 is a graph showing the anti-bacterial effectiveness of the anti-microbial agent mafenide by percentage of testing stratum weight to determine the amount of cleared zone around the testing stratum at predetermined concentrations of the anti-microbial agent mafenide, while the test organism utilized is *Pseudomonas aeruginosa;*
Figure 7:
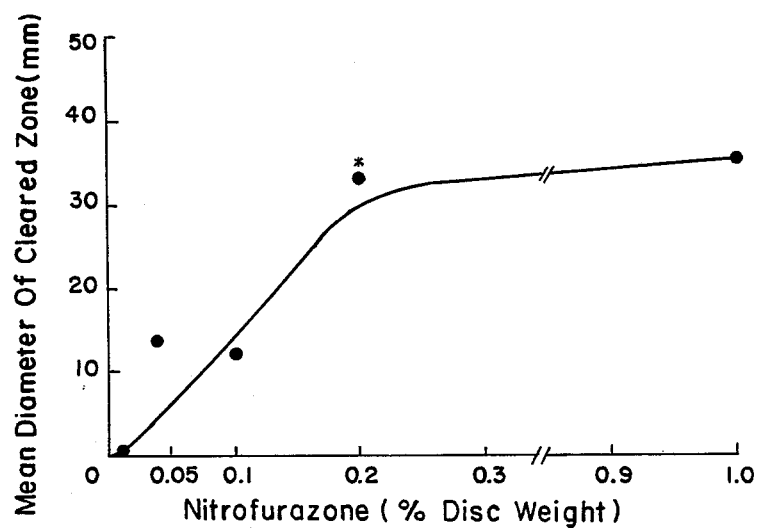
FIG. 7 is a graph showing the anti-bacterial effectiveness of the drug nitrofurazone which illustrates the cleared zone of anti-microbial contaminants relative to the concentration of the anti-microbial agent nitrofurazone by weight of the testing stratum, which test organism may comprise *Staphylococcus aureus.
Figure 8:
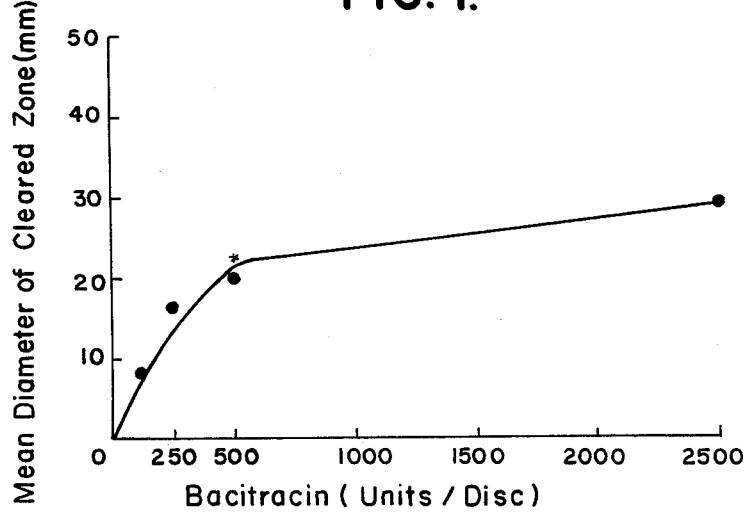
* and FIG. 8 is also a graph showing the anti-bacterial effectiveness of the anti-microbial agent bacitracin in units per stratum as measured by the amount of cleared zone around the testing stratum based upon the amount of concentration of the anti-microbial agent bacitracin in the particular testing stratum. The test organism is an isolate of *Staphylococcus aureus.*

In evaluating the formulations of the compound as set forth in Tables I and II above, reference is made to FIGS. 3 and 5 of the drawings in connection with FIGS. 6-8, in order to understand how the various anti-microbial agents in the examples performed relative to a specific microbial contaminant. In each case tested, an isolate of *S. Aureus* served as a test organism or microbial contaminant.

In the Tables I and II formulations tested with this micro-organism, it was seen that No. 1 silver sulfadiazine, No. 3 nystatin, No. 5 silver nitrate, and No. 7, the control disc, had no effect whatsoever on the microbial contaminant, and thus for all practical purposes, they were ineffective in treating this micro-organism or contaminant. On the other hand, No. 2 mafenide, No. 4, nitrofurazone, and No. 6 bacitracin killed or inhibited the anti-microbial contaminant, as will be described hereafter in connection with FIGS. 6-8 of the drawing.

FIGS. 6-8 show the effects of variance of the concentration of the anti-microbial agent in the synthetic matrix delivery system relative to the size of the cleared areas surrounding each of test disc No. 2 mafenide, test disc No. 4 nitrofurazone, and test disc No. 6 bacitracin. The clear area 26 around each disc represents killed or destroyed contaminants, whereas a slightly shaded area 28 around the clear area 26 represents bacterial or contaminant growth inhibition, rather than destruction.

In FIG. 6, the effect of varying mafenide concentration as a percentage of disc weight from 1% to 10% indicated a change in the diameter of the cleared area surrounding the test disc. Between 1% and 5% concentration or percentage disc weight, the cleared area as shown by the graph in FIG. 6 showed a marked increase. However, no change in the clear zone surrounding the test disc was noted when the drug content was varied from 5% to 10% of the disc weight. As seen in FIG. 6 of the drawings, the graph shows little or no increase in the mean diameter of cleared zone above 5% of the disc weight. Therefore, an optimum amount of anti-microbial agent or drug chosen as the concentration for the test disc was selected at 5%. Each point shown in the graph of FIG. 6 represents the mean of three separate tests which were performed in preparing the graph. The asterisk represents the optimum amount of drug selected, which, in this case, was 5%.

FIG. 5 of the drawing illustrates the partially cleared, and the partially inhibited zone diameter for *S. Aureus* cultures surrounding the test disc including the drug nitrofurazone. It will be seen that the anti-microbial agent nitrofurazone did not function as well as mafenide since the mean diameter of cleared zone (mm) did not rise above about 35 mm, whereas the cleared zone in the mafenide compound had a mean diameter of about 45 mm. The graph in FIG. 7 further demonstrates that the nitrofurazone level in the test disc is not strongly affected by varying drug concentrations above 0.2%, and therefore, the asterisk representing the concentration use in the test disc is shown as being placed at the 0.2% level in FIG. 7 of the drawing.

In FIG. 8 of the drawings, the changes in the clear zone diameter for *S. Aureus* cultures is shown where the bacitracin concentration varies from 100 to 2500 units per test disc. For 500-2500 units per test disc, the mean diameter of clear zone (mm) increased 50%, from 20 mm to 30 mm. Since only minor changes in the clear area will be produced over this range by variations in the bacitracin incorporated in the test disc, 500 units of bacitracin/gram were incorporated in the test disc, as shown by the asterisk in FIG. 8 of the drawings representing the concentration used in the test disc.

From the above examples, it was established that the anti-microbial agent mafenide having 5% of the disc weight exhibited a mean diameter of cleared zone of about 45-50 mm for the *S. Aureus* microbial contaminant. As can be seen by comparing the FIG. 6-8 chart results, in conjunction with the FIG. 5 physical manifestation of the zones of reaction, this was substantially greater than 30-35 mm cleared area for nitrofurazone and the 25-30 mm cleared area for bactracin. From the results, it would be concluded that the anti-microbial agent mafenide, for this particular microbial contaminant, exhibited best effectiveness.

With the proposed invention, test results are obtained within about 16-24 hours after the wound site is sampled. This is a much shorter time period than is normally required for identifying the microbial contaminant using conventional procedures, and therefore effective treatment can be initiated much earlier. Since the anti-microbial sensitivity test is also simple to administer, it is envisioned that para-professionals such as nurses could administer the test kit to patients, particularly those with dicubitus ulcers. It would also be possible to use the anti-microbial sensitivity test in clinical dermatology, where indicated, and further, microbiology laboratories could also use this anti-microbial sensitivity test for a rapid determination of the drug of choice ro treat a particular microbial contaminant.

It is also contemplated that an anti-microbial sensitivity or diagnostic test kit may be provided which would include a variety of testing stratum incorporating certain anti-microbial agents, as well as the agar and media described above. Culture tubes incorporating the pre-moistened saline swab as well as the Petri plates may also be part of the diagnostic kit, although the heater block and incubator may be supplied separately.

In addition to those anti-microbial agents which were tested in the examples described above, it will be possible to incorporate additional active anti-microbial agents in the synthetic matrix delivery system to evaluate the anti-microbial agent effectiveness relative to a particular microbial contaminant or strain. Such additional products would include agents such as gentamicin, amphotericin B, cesium nitrate, and other anti-microbial agents now or hereafter developed. It is also anticipated that special test plates with additional anti-microbial agents not described may be requested by a particular physician encountering an unknown or particularly difficult microbial contaminant.

In view of the above, use of the anti-microbial sensitivity test and testing stratum of the present invention provides a highly sensitive and accurate determination of the anti-microbial drug(s) of choice for the treatment of wounds or infection in a relatively short period of time after the wound-site is sampled. The test and testing stratum also has the ability to selectively eliminate those anti-microbial agents or drugs which are ineffective against the microbial contaminant in a specific wound in order to allow the clinician and doctor to exclude inactive drugs or agents from the patient's treatment protocol, while selecting those particular agents that are most effective against the specific microbial contaminant in the patient's wound infections.

As can thus be seen, other objects of this invention are achieved and other advantage results are obtained.

As various changes could be made in the above constructions, processes, or methods without departing from the scope of the invention, it is intended that all matter contained in the above description or shown in the accompanying drawings shall be interpreted as illustrative and not in a limiting sense. In particular, it is possible to present the diagnostic kit with the agar already poured on a plate. The test discs would be applied in a fixed pattern on top of/or into the agar prior to or after application of the test microbial contaminants. This would further simplify the technology.

Having thus described the invention what is claimed and desired to be secured by Letters Patent is:

1. An anti-microbial sensitivity testing stratum for evaluating the sensitivity of anti-microbial agents relative to identifiable microbial contaminants, said stratum comprising a particulate, hydrophilic, water swellable polymer of an acrylate or acrylamide ranging approximately from 20%–55% by weight of said stratum; a hydrogen bonding plasticizer of dimethysulfoxide ranging approximately up to 20% by weight of said stratum; an inert, non-toxic water miscible organic solvent of polyethylene glycol ranging approximately 20%–65% by weight of said stratum; and an anti-microbial agent, constituting the remainder by weight of said stratum.

2. The anti-microbial sensitivity testing stratum as defined in claim 1 wherein said polymer is poly (2-hydroxyethylmethacrylate), said plasticizer is dimethyl sulfoxide, and said solvent is polyethylene glycol having a molecular weight of about 200–2000.

3. The anti-microbial sensitivity testing stratum as defined in claim 2 wherein said anti-microbial agent has a range approximately up to 10% by weight of said stratum.

4. The anti-microbial sensitivity testing stratum as defined in claim 3 wherein said anti-microbial agent is silver sulfadiazine having about 1% by weight of said stratum.

5. The anti-microbial sensitivity testing stratum as defined in claim 3 wherein said anti-microbial agent is mafenide having about 5% by weight of said stratum.

6. The anti-microbial/sensitivity testing stratum as defined in claim 3 wherein said anti-microbial agent is nystatin having about 1.7% by weight of said stratum.

7. The anti-microbial sensitivity testing stratum as defined in claim 3 wherein said anti-microbial agent is nitrofurazone having about 0.2% by weight of said stratum.

8. The anti-microbial sensitivity testing stratum as defined in claim 3 wherein said anti-microbial agent is silver nitrate having about 0.5% by weight of said stratum.

9. The anti-microbial sensitivity testing stratum as defined in claim 3 wherein said anti-microbial agent is bacitracin having about 0.83% by weight of said stratum.

10. The anti-microbial sensitivity testing stratum as defined in claim 2 wherein said anti-microbial agent is gentamicin.

11. The anti-microbial sensitivity testing stratum as defined in claim 2 wherein said anti-microbial agent is amphotericin B.

12. The anti-microbial sensitivity testing stratum as defined in claim 2 wherein said anti-microbial agent is cesium nitrate.

13. The process of evaluating the sensitivity of different anti-microbial agents relative to a particular microbial contaminant(s) which includes the steps of providing a plurality of anti-microbial sensitivity testing stratum as defined in claim 2, each having a sustained release anti-microbial agent of different composition therein, positioning each of the testing stratum on a sterile plate in spaced relationship to one another, subjecting each of the testing stratum and intermediate portions of the sterile plate to the microbial contaminant being tested, and evaluating any zones of inhibition over and around each of said anti-microbial agent in inhibiting the growth of the particular microbial contaminant(s).

* * * * *

UNITED STATES PATENT AND TRADEMARK OFFICE
CERTIFICATE OF CORRECTION

PATENT NO. : 4,820,292
DATED : April 11, 1989
INVENTOR(S) : Korol, et al.

It is certified that error appears in the above—identified patent and that said Letters Patent is hereby corrected as shown below:

Front page, title of assignee, change "Enguay" to

---Enquay---.

Signed and Sealed this

Third Day of October, 1989

Attest:

DONALD J. QUIGG

*Attesting Officer*  *Commissioner of Patents and Trademarks*